United States Patent [19]

Toukan

[11] 4,258,197
[45] Mar. 24, 1981

[54] MANUFACTURE OF SULFENAMIDES
[75] Inventor: Sameeh S. Toukan, Schuylkill, Pa.
[73] Assignee: Pennwalt Corporation, Philadelphia, Pa.
[21] Appl. No.: 47,176
[22] Filed: Jun. 8, 1979
[51] Int. Cl.³ .......................................... C07D 277/80
[52] U.S. Cl. .................................................. 548/167
[58] Field of Search ................. 260/306.6 A; 548/167
[56] References Cited

U.S. PATENT DOCUMENTS

| | | | |
|---|---|---|---|
| 2,268,467 | 12/1941 | Ashworth | 548/167 |
| 2,271,834 | 2/1942 | Carr | 548/167 |
| 2,354,427 | 7/1944 | Carr | 548/167 |
| 2,419,283 | 4/1947 | Paul et al. | 548/167 |
| 3,600,398 | 8/1971 | Suarz et al. | 548/167 |

FOREIGN PATENT DOCUMENTS

| | | | |
|---|---|---|---|
| 655668 | 8/1951 | United Kingdom | 548/167 |
| 772582 | 4/1957 | United Kingdom | 548/167 |

*Primary Examiner*—Donald G. Daus
*Assistant Examiner*—D. B. Springer

[57] ABSTRACT

Processes for the manufacture of sulfenamides by the oxidation of a mixture of 2-mercaptobenzothiazole and the appropriate amine in a critical amount of water and/or organic solvent produces a pure product of good quality and high yield. The amount of water should be in the range of from 10 to 30% by weight based on the total reaction mixture.

5 Claims, No Drawings

MANUFACTURE OF SULFENAMIDES

BACKGROUND OF THE INVENTION

The present invention relates to a general process for the manufacture of sulfenamides.

2-benzothiazole sulfenamides have become commercially important as rubber vulcanization accelerators, lubricating oil additives, and fungicides. Their most important commercial utilization is their use as accelerators in rubber vulcanization; in order to have efficient application in such a process, the sulfenamides accelerators must be of high purity.

The preparation of sulfenamides is well known in the prior art. The most widely used process involves the oxidation of 2-mercaptobenzothiazole (called MBT) in the presence of the desired amine. The oxidation agent can be sodium hypochlorite, a halogen, hydrogen peroxide, potassium persulfate, potassium dichromate, etc. The prior art processes for making the sulfenamides are normally complicated or produce a crude product that must be further purified. U.S. Pat. No. 3,600,398 teaches the use of a molar ratio of MBT to the amine in the range of at least 1:8 to 1:10 ratio in order to obtain the sulfenamide in pure form in excellent yield. In the present invention, surprisingly, a ratio of 1:4 gave a 91.4% pure product while a ratio of 1:5 afforded a 99.4% pure sulfenamide. More surprisingly, when the ratio of MBT to amine was raised to 1:7, the purity of the product fell to 98% (see Table II d, e, f).

Although part of the amine could be recovered according to known procedures, the less amine used the more economical the process will be. U.S. Pat. No. 2,419,283 teaches the oxidation process for making the sulfenamides by using additional material such as $Na_2SO_4$ or NaCl which also produces impurities in the final product. British Pat. No. 772,582 teaches a complex oxidation method for producing the sulfenamides that reuires constant pH correction, addition of NaOH and the determination of potential. British Pat. No. 655,668 teaches an oxidation method limited to primary amines and an excess of water. Example 14 illustrates the failure of this process when the secondary amine, morpholine, and a comparatively large amount of water were used. No product could be isolated from this process.

The present invention overcomes the above mentioned problems of the prior art processes since there is no addition of strong alkaline solutions or strong acids that will create a need for the adjustment of the pH. The present invention involves a general process which is not limited to primary amines yet it is a simple and inexpensive process that does not require many steps. By using this simple process, it is possible to prepare most of the sulfenamide derivatives, if not all, which previously were prepared by distinct individual processes. Furthermore, the fact that these sulfenamides are produced in high yields and purity without the need for purification is an important advantage of this invention.

SUMMARY OF THE INVENTION

The present invention is directed to an improved process for the manufacture of sulfenamides comprising:

cooling 1.5–4 moles of a primary or secondary amine to a temperature range of 0°–10° C. and adding said amine dropwise to a previously cooled (8°–12° C.) MBT-water or MBT-solvent mixture containing one mole of MBT, while maintaining a temperature below 20° C.;

adding 1.5–2 moles of an oxidizing agent slowly to the mercaptobenzothiazole-amine-water mixture while maintaining the temperature of the solution in the range of 25° to 60° C. until the oxidation is completed;

cooling the oxidized reaction mixture to about 5° to 15° C. whereby the sulfenamide product precipitates; and recovering the sulfenamide product in substantially pure form.

DETAILED DESCRIPTION OF THE INVENTION

According to the present invention, the sulfenamides are prepared by the oxidation of a mixture of 2-mercaptobenzothiazole (called MBT) and the appropriate primary or secondary amine in a measured amount of water or organic solvent, preferably ethylene glycol monobutyl ether solvent (called butyl cellosolve). This invention also applies to the preparation of the sulfenamides starting with an intermediate product 2,2-dithiobisbenzothiazole which is an intermediate product in the course of the reaction starting with the MBT.

Addition of the amine to the MBT is accomplished by first cooling the amine to 0° C. and the MBT-water mixture to 8°–12° C., preferably to 10° C. The amine is then added dropwise to the MBT-H$_2$O mixture while the temperature is kept below 20° C. and preferably at 10° to 12° C. If the addition is reversed, then the MBT is added in powdered form in small aliquots to the cold-mixture of the amine and water at 5° to 10° C.

When no organic solvent is used, the molar ratio of MBT to the amine is in the range of 1:3 to 1:5 and preferably 1:4. When the reaction is carried out in the presence of an organic solvent, the preferred molar ratio of MBT to amine is only 1:1.5 to 1:2. The amount of water used to start the reaction of the amine with MBT is critical and can be in the range of 10 to 30% and preferably 10 to 20% of the total combined weight of the reactants, i.e., weight of MBT, the amine, the oxidizing agent and the water in question. This does not include any additional water used as a solvent for the oxidizing agent or a diluent during the process of preparing the sulfenamide.

Similarly, if a solvent is used instead of water for the MBT-amine mixture, the amount should be enough to give 20 to 60% slurry of MBT in that solvent and preferably 25 to 35%. Thus, the sulfenamide derivatives are prepared in excellent yield and high purity.

The oxidizing agent could be any of the commonly water soluble agents such as the halogens, alkali metal hypochlorites, hydrogen peroxide, the dichromate metal salts, the perchlorate metal salts, etc. Sodium hypochlorite is a convenient oxidizing agent for the reactions of this invention because it is commercially available as a 15% aqueous solution and relatively inexpensive. The molar ratio of MBT to sodium hypochlorite is in the range of 1:1.25 to 1:2 and preferably 1:1.5.

The sodium hypochlorite solution is added slowly and carefully so that the temperature is maintained within a small range of variation. Before the addition of the oxidizing agent, the MBT-amine-water mixture is stirred at ambient temperature for about 15 to 30 minutes, then heated slowly to 25° to 60° C. (preferably 47° to 50° C.) before adding the sodium hypochlorite solution. The preferred range of temperature should be maintained throughout the addition. Addition time is usually about 2 hours. After addition is completed, a KI/starch test should be positive; if negative, more sodium hypochlorite is added. The reaction mixture is then stirred at the same preferred range of temperature for 1 to 2 hours to insure complete oxidation. Lower temperatures will result in incomplete oxidation and impure product while higher temperatures reduce the overall yields.

The excess oxidizing agent is usually destroyed by adding slowly over a 5 to 10 minute period enough of $Na_2SO_3$ dissolved in a large amount of water to the hot reaction mixture. A negative test should be obtained when a KI/starch test paper is treated with an acidified sample of reaction mixture. The reaction mixture is then cooled to about 5° to 15° C. (preferably 10° C.) followed by filtration of the crystalline solid. The filtered solid is finally thoroughly washed several times with cold water (about 10° C.) followed by tap water and in some cases warm water (about 40° C.) until the last washing is neutral to litmus paper. Air drying is usually sufficient to remove most of the water from the product. However, drying under vacuum at about 40° to 50° C. results in a completely dry product.

The present invention will be further illustrated by the following examples which are set forth merely to illustrate the invention but are not intended to limit the practice of this invention thereto.

EXAMPLE 1

Preparation of 2-(4-morpholinylthio)benzothiazole

A well-stirred slurry of 42.6 g (0.25 mole; 98% pure) of MBT in 100 ml of ethylene glycol monobutyl ether (called butyl cellosolve) was cooled to 10° C.; 32.6 g of morpholine (0.375 mole; 50% excess) was added dropwise to the stirred slurry while the temperature was kept at 12°–15° C. After addition was complete, the ice bath was removed and the mixture was stirred at ambient temperature for 0.5 hour and then heated to 47°–50° C. Stirring was continued at this temperature for an additional 0.5 hour.

A 15.8% solution of NaOCl in water (177.0 g; 0.375 mole) was added dropwise to the stirred heated mixture while the temperature was kept at 47°–50° C. Addition was completed in 1.5 hours. An acidified sample of reaction mixture gave a positive test with starch-iodide paper. The mixture was stirred at the same temperature range of 47°–50° C., for one hour. The heating bath was removed and, without outside cooling of reaction mixture, a solution of 10.0 g of $Na_2SO_3$ in 700 ml of water was added slowly over a period of about 10 minutes. Another sample of reaction mixture was tested with starch-iodide paper and was found negative, otherwise more $Na_2SO_3$ solution would have been added. The mixture was cooled to 10° C. and the light tan precipitated solid was filtered off, washed to remove the alkaline solution with 4×250 ml of ice-cold water and again with 4×250 ml of tap water, until the washings were neutral to litmus paper. After air-drying overnight and vacuum-drying at about 50° C. for 5 hours, 58.0 g (92% yield) of a tan solid, m. p. 83°–85° C., were obtained. An infrared spectrum was consistent with the desired structure.

Anal.-Purity, 99.7%; Sulfur, 25.4% (calc'd 25.35%).

EXAMPLES 2 to 8

All were prepared following the procedure given in Example 1. These Examples illustrate the effect of solvent (butyl cellosolve) and concentration of the base on the yield and purity of product; see Table I:

TABLE I

Effect of Solvent and Concentration of the Base on the Yield and Purity of Product

| Ex. # | Moles MBT | Molar Excess of Morpholine | Moles NaOCl | Ml Solvent | % Yield | % Purity | M. P. Lit. m. p. 84–86° C. |
|---|---|---|---|---|---|---|---|
| 1 | 0.25 | 50% | 0.375 | 100 | 92 | 99.7 | 83–85° C. |
| 2 | 0.25 | 50% | 0.375 | 150 | 90 | 98.8 | 82–86° C. |
| 3 | 0.25 | 50% | 0.375 | 50 | 85.5 | 96.5 | 83–86° C. |
| 4 | 0.25 | 50% | 0.375 | 25 | 90 | 92.6 | 80–84° C. |
| 5 | 0.25 | 2% | 0.375 | 150 | 83 | — | 83–85° C. |
| 6 | 0.25 | 10% | 0.375 | 150 | 83 | — | 81–84.5° C. |
| 7 | 0.25 | 20% | 0.375 | 150 | 83 | — | 83–86° C. |
| 8 | 0.25 | 40% | 0.375 | 150 | 88 | — | 82–85° C. |

EXAMPLE 9

Preparation of N-tert-Butyl-2-benzothiazolesulfenamide

To a well-stirred ice-cooled slurry mixture of 42.6 g of MBT (0.25 mol; 98% pure) in 150 ml of butyl cellosolve were added dropwise 36.6 g of tert-butylamine (0.5 mole) while the temperature was kept below 15° C. After stirring for about 10 minutes, the mixture was heated gradually to 35° C. over a period of 0.5 hour.

A 15.8% solution of NaOCl in water (177.0 g; 0.375 mole) was added dropwise at 35°–40° C. over a period of 2 hours. A sample of the reaction mixture was tested with KI/starch paper and was positive. The reaction mixture was stirred at the same temperature range of 35°–40° C. for 1.5 hours. The heating bath was removed and a solution of 5.0 g of $Na_2SO_3$ in 250 ml of water was carefully added over a period of about 10 minutes. Another sample of reaction mixture gave a negative test with KI/starch paper. After cooling to 10° C. and diluting with 500 ml of ice-cold water, the insoluble solid was collected by filtration, washed with 4×250 ml of ice-cold water and 4×250 ml of warm water at 40° C. and air-dried to afford 49.7 g (83% yield) of a light tan solid, m. p. 106°–109° C. An infrared spectrum was consistent with the desired structure.

Anal.-Purity, 97.4%; Sulfur, 27.2% (calc'd 26.9%).

EXAMPLE 10

Preparation of N-Cyclohexyl-2-benzothiazolesulfenamide

By following the same procedure as in Example 9 and using 42.6 g (0.25 mole) of MBT (98% pure), 49.6 g (0.5 mole) of cyclohexylamine, 177.0 g (0.375 mole) of NaOCl solution (conc. 15.8%) and 150 ml of butyl cellosolve; a light tan solid, m. p. 99°–103° C. was obtained in 83% yield. An infrared spectrum showed characteristic absorption.

Anal.-Purity, 97.6%; Sulfur, 24.4% (cal'd 24.25).

EXAMPLE 11

Preparation of N-Isopropyl-2-benzothiazolesulfenamide

By following the same procedure as in Example 9 and reacting 42.6 g (0.25 mole) of MBT (98% pure) with 29.6 g (0.5 mole) of isopropylamine and 177.0 g (0.375 mole) of NaOCl solution (conc. 15.8%) in 150 ml of butyl cellosolve at 45°–50° C.; a white solid, m. p. 91°–94° C., was obtained in 85.5% yield. An infrared spectrum showed the characteristic absorption.

Anal.-Purity, 99.1%; Sulfur, 29.0% (calc'd 28.5%).

EXAMPLE 12

Preparation of N,N-Diisopropyl-2-benzothiazolesulfenamide

A total of 42.6 g (0.25 mole; 98% pure) of MBT was added in small portions to a stirred, cooled mixture (5° C.) of 50.6 g (0.50 mole) of diisopropylamine and 75 ml of butyl cellosolve while the temperature was kept below 20° C. The resulting cold slurry was stirred at ambient temperature for 0.5 hour, then heated slowly up to 55° C. over a period of 15 minutes, and finally cooled to 20° C.

A total of 200.0 g (0.425 mole) of a 15.8% NaOCl solution was added dropwise at 20°–25° C. over a period of 2.5 hours. After the addition was complete, and a KI/starch test was found to be positive, the mixture was stirred in the same temperature range for one hour and heated at 45°–50° C. for an additional 45 minutes to insure complete oxidation. The rest of the workup was completed as described in Example 1 to afford 50.2 g (75% yield) of a yellowish tan solid, m. p. 55°–58° C. The infrared spectrum was consistent with the desired structure.

Anal.-Purity, 95.7%; Sulfur, 23.6% (calc'd 24.07%).

EXAMPLE 13

Preparation of the Morpholino Derivative without Organic Solvent

A stirred mixture of 42.6 g (0.25 mole; 98% pure) of MBT in 30 ml of water was cooled to 10° C. One mole (87.1 g) of morpholine was cooled to −5° C. and then added dropwise to the MBT-H$_2$O cold mixture over a period of 0.5 hour while the temperature was kept below 20° C. After being stirred for 15 minutes at ambient temperature, the mixture was gradually heated to 45° C. over a period of 0.5 hour.

The rate of addition of 177.0 g (0.375 mole) of 15.8% sodium hypochlorite solution as well as the rest of the experimental workup were the same as in Example 1. A tan solid, m. p. 82°–85° C. and weighing 59.2 g, was obtained. The yield was 94%.

Anal.-Purity, 95.9%; Sulfur, 24.9% (calc'd 25.35%).

EXAMPLE 14

Attempted Preparation of the Morpholino Derivative Using Large Excess of Water A total of 42.6 g (0.25 mole; 98% pure) of MBT was added to a stirred solution of 87.1 g (1.0 mole) of morpholine in 150 ml of distilled water while keeping the temperature below 30° C. The mixture was heated to 45° C. followed by the dropwise addition of 165 g (0.35 mole) of 15.8% sodium hypochlorite solution at a temperature range of 45°–50° C. over a period of 2 hours. The rest of the experimental workup was the same as in Example 1. There was obtained 51.7 g (82% yield) of a light tan solid, m. p. 73°–138° C., indicating a very impure product or a mixture of several products.

EXAMPLE 15

Preparation of N-Isopropyl-2-benzothiazolesulfenamide

By following the same procedure as in Example 13, using H$_2$O as the solvent, a 95% yield of pale greenish gray solid, m. p. 93°–96° C., was obtained.

Anal.-Purity, 95.3%; Sulfur, 26.4% (calc'd 28.5%).

EXAMPLE 16

Preparation of N-tert-Butyl-2-benzothiazolesulfenamide

A total of 42.6 g (0.25 mole; 98% pure) of MBT was added in small portions to a stirred cooled mixture (5° C.) of 73.1 g (1 mole) of tert-butylamine and 25.5 ml of water, while the temperature was kept below 20° C. After the addition was completed, the mixture was heated to 45°–50° C.; 177.0 g (28.0 g; 0.375 mole) of NaOCl solution (15.8% conc.) were added dropwise at 45°–50° C. over a period of 2 hours. After a KI/starch test was found positive; the mixture was stirred in the same temperature range for 1.5 hours to insure complete oxidation. The rest of the workup was the same as that of Example 1, except that in addition to washing the crude product with cold water, it was further washed with an equal amount of warm water (40° C.). A pale greenish gray solid weighing 54.6 g (92% yield) was obtained. Its m. p. was 106°–109° C. and the IR spectra indicated characteristic absorptions.

Anal.-Purity, 91.4%; Sulfur, 26.9% (calc'd 26.9%).

EXAMPLE 17

Preparation of N-Cyclohexyl-2-benzothiazolesulfenamide

By following the procedure of Example 15 and washing the crude product with ice-cold water as well as with tap water, a 92% yield of a pale greenish solid, m. p. 98°–101° C., was obtained.

Anal.-Purity, 97.6; Sulfur, 24.7 (calc'd 24.25).

EXAMPLE 18

Preparation of N,N-Diisopropyl-2-benzothiazolesulfenamide

A total of 42.6 g of MBT(0.25 mole; 98% pure) as added in small portions to an ice-cold stirred mixture (5° C.) of 101.2 g (1.0 mole) of diisopropylamine and 20 ml of water while the temperature was kept below 20° C. After the addition was completed, the mixture was warmed up to 30° C. and 200.0 g (31.6 g; 0.425 mole) of NaOCl solution (15.8% conc.) were added dropwise at 28°–30° C. over a period of 2.5 hours. The rest of the workup was the same as that of Example 1. A light tan solid was obtained, weighing 54.5 g (82% yield) with a m. p. of 55°–57° C. and IR spectrum consistent with the desired structure.

Anal.-Purity, 96.8%; Sulfur, 24% (calc'd 24.07%).

Running the reaction at 35°–40° C., afforded 54.0 g (81% yield) of a light tan solid having the same physical properties as above.

Anal.-Purity, 98.3%; Sulfur, 23.5% (calc'd 24.07%).

TABLE II

Effect of the Amine Concentration on the Yield and Purity of the Sulfenamides in a Non-organic Solvent System

|     |            | MBT:Amine Ratio | % Yield | % Purity |
|-----|------------|-----------------|---------|----------|
| (a) | Morpholino | 1:4             | 94      | 95.9     |

TABLE II-continued

Effect of the Amine Concentration on the Yield and Purity of the Sulfenamides in a Non-organic Solvent System

|     | MBT:Amine | Ratio | % Yield | % Purity |
|-----|-----------|-------|---------|----------|
| (b) | "         | 1:3   | 90.5    | 93.6     |
| (c) | "         | 1:2   | 74.5    | N.A.     |
| (d) | t-Butyl   | 1:4   | 92      | 91.4     |
| (e) | "         | 1:5   | 92      | 99.4     |
| (f) | "         | 1:7   | 92.3    | 98.0     |

What is claimed is:

1. A process for the manufacture of 2-benzothiazole-sulfenamides consisting essentially of:

adding 10 to 30 percent by weight of a member selected from the group consisting of water, 20 to 60 percent by weight of ethylene glycol monoalkyl ether solvent, and a mixture thereof to one mole of 2-mercaptobenzathiazole and cooling the mixture to 8°-12° C.;

adding dropwise 1.5 to 4 moles of a primary or secondary amine selected from the group consisting of morpholine, tert-butylamine, isopropylamine, diisopropylamine and cyclohexylamine to the mercaptobenzothiazole-water mixture while maintaining a temperature below 20° C.;

adding 1.5 to 2 moles of an oxidizing agent selected from the group consisting of chlorine, alkali metal hypochlorites, and hydrogen peroxide slowly to the mercaptobenzothiazoleamine-water mixture while maintaining the temperature of the solution in the range of 25° to 60° C. until the oxidation is completed;

cooling the oxidized reaction mixture to about 5° to 15° C. whereby the sulfenamide product precipitates; and recovering the sulfenamide product in substantially pure form.

2. A process according to claim 1 in which the oxidizing agent is an alkali metal hypochlorite and which is carried out in a range of 20°-60° C.

3. A process according to claim 1 where the oxidation is carried out in an entirely aqueous medium.

4. A process according to claim 3 where the organic solvent is ethylene glycol monobutyl ether.

5. A process according to claim 1 where the oxidation is carried out in a mixture of water and ethylene glycol monoalkyl ether solvent.

* * * * *